(12) United States Patent
Cha et al.

(10) Patent No.: US 7,563,457 B2
(45) Date of Patent: Jul. 21, 2009

(54) NANOPARTICLE ASSEMBLED HOLLOW SPHERES

(75) Inventors: Jennifer Cha, Berkeley, CA (US); Timothy J. Deming, Summerland, CA (US); Galen D. Stucky, Goleta, CA (US); Michael Wong, Houston, TX (US); Henrik Birkedal, Goleta, CA (US); Michael H. Bartl, Santa Barbara, CA (US); Jan L. Sumerel, Goleta, CA (US)

(73) Assignee: The Regents of the University of California, Oakland, CA (US)

( * ) Notice: Subject to any disclaimer, the term of this patent is extended or adjusted under 35 U.S.C. 154(b) by 339 days.

(21) Appl. No.: 10/263,271

(22) Filed: Oct. 2, 2002

(65) Prior Publication Data

US 2003/0082237 A1    May 1, 2003

Related U.S. Application Data

(60) Provisional application No. 60/326,870, filed on Oct. 2, 2001, provisional application No. 60/360,939, filed on Mar. 1, 2002.

(51) Int. Cl.
    *A61K 9/16*    (2006.01)
(52) U.S. Cl. .................. 424/491; 424/489; 428/402; 977/705
(58) Field of Classification Search ................ 424/489, 424/400, 451, 497, 502, 490; 427/213.31; 210/679
    See application file for complete search history.

(56) References Cited

U.S. PATENT DOCUMENTS

| | | | |
|---|---|---|---|
| 4,285,819 A | * | 8/1981 | Yen et al. .............. 210/679 |
| 4,861,627 A | * | 8/1989 | Mathiowitz et al. ..... 427/213.31 |
| 5,840,340 A | * | 11/1998 | Milstein |
| 6,123,965 A | * | 9/2000 | Jacob et al. |
| 6,238,701 B1 | * | 5/2001 | Muller et al. ............ 424/489 |
| 6,395,029 B1 | * | 5/2002 | Levy et al. |
| 6,479,146 B1 | * | 11/2002 | Caruso et al. ............ 428/403 |
| 6,497,729 B1 | * | 12/2002 | Moussy et al. ........... 623/23.57 |
| 6,660,381 B2 | * | 12/2003 | Halas et al. ............. 428/403 |

FOREIGN PATENT DOCUMENTS

WO    WO 94/08627    *    4/1994

OTHER PUBLICATIONS

Zasadzinski, J.A. et al. "Complex vesicle-based structures," *Current Opinion in Colloid & Interface Science* 6(1):85-90 (2001).

(Continued)

*Primary Examiner*—Eric E. Silverman
(74) *Attorney, Agent, or Firm*—Berliner & Associates

(57) ABSTRACT

A design strategy for constructing hierarchically structured materials using nanoparticles and synthetic biopolymers has been developed. Block copolypeptides or homopolymer polyelectrolytes are used as structure-directing agents to arrange nanoparticles (composed of metals, metal non-oxides, metal oxides, or organics) into unusual microstructures, such as spheres, "apples" and "cups." Hollow spheres can be made wherein nanoparticles of one composition are spatially oriented completely interior or exterior to nanoparticles of a second composition. These aggregates contain nanoparticles only in the shell walls, and maintain their hollowness upon calcination. These shapes can also be fabricated into films. These robust materials are anticipated to have great promise in applications that require surface catalysis, magnetic/electronic/optic properties, transport capabilities, and combinations thereof, such as drug delivery, packaging, catalysis, and sensors.

6 Claims, 6 Drawing Sheets

OTHER PUBLICATIONS

Kokkona, M. et al. "Stability of SUV liposomes in the presence of cholate salts and pancreatic lipases: effect of lipid composition" *European Journal of Pharmaceutical Sciences* 9:245-252 (2000).

Bogunia-Kubik, K. et al. "From molecular biology to nanotechnology and nanomedicine," *Biosystems* 65:123-138 (2002).

Sershen, S.R. et al. "Temperature-sensitive polymer-nanoshell composites for photothermally modulated drug delivery," *J. Biomed. Mater. Res.* 51(3):293-298 (2000).

Terrettaz, S. et al. "Stable self-assembly of a protein engineering scaffold on gold surfaces,"0 *Protein Science* 11(8):1917-1925 (2002).

Braden, B.C. et al. "X-ray crystal structure of an anti-Buckminsterfullerene antibody Fab fragment: Biomolecular recognition of $C_{60}$," *Proc. Natl Acad. Sci. USA* 97(22):12193-12197.

Alivisatos, A.P. "Semiconductor Clusters, Nanocrystals, and Quantum Dots," *Science* 271:933-937 (1996).

Mirkin, C.A. et al. "A DNA-based method for rationally assembling nanoparticles into macroscopic materials," *Nature* 382:607-609 (1996).

Shenton, W. et al. "Directed Self-Assembly of Nanoparticles into Macroscopic Materials Using Antibody-Antigen Recognition," *Adv. Mater.* 11(6):449-452 (1999).

Brousseau, III, L.C. et al. "Assembly of Phenylacetylene-Bridged Gold Nanocluster Dimers and Trimers," *Adv. Mater.* 11(6):447-449 (1999).

Zhong, Z. et al. "Preparation of Mesoscale Hollow Spheres of $TiO_2$ and $SnO_2$ by Templating Against Crystalling Arrays of Polystyrene Beads," *Adv. Mater.* 12(3):206-209 (2000).

Wong, M.S. et al. "Assembly of Nanoparticles into Hollow Spheres Using Block Copolypeptides," *Nano Letters* 2(6):583-587 (2002).

Deming, T.J. "Facile synthesis of block copolypeptides of defined architecture," *Nature* 390:386-389 (1997).

Bruchez, Jr., M. et al. "Semiconductor Nanocrystals as Fluorescent Biological Labels," *Science* 281:2013-2016 (1998).

Eisler, H.J. et al. "Color-selective semiconductor nanocrystal laser," *Applied Physics Letters* 80(24):4614-4616 (2002).

Huynh, W.U. et al. "Hybrid Nanorod-Polymer Solar Cells," *Science* 295:2425-2427 (2002).

Kazes, M. et al. "Lasing from Semiconductor Quantum Rods in a Cylindrical Microcavity," *Advanced Materials* 14(4):317-321 (2002).

Kilmov, V.I. et al. "Optical Gain and Stimulated Emission in Nanocrystal Quantum Dots," *Science* 290:314-317 (2000).

Yokoyama, H. "Physics and Device Applications of Optical Microcavities," *Science* 256:66-70 (1992).

Fan, X. et al. "Enhanced spontaneous emission from semiconductor nanocrystals embedded in whispering gallery optical microcavities," *Science* 64:115310-115310-5 (2001).

Klimov, V.I. et al. "Ultrafast Carrier Dynamics, Optical Amplification, and Lasing in Nanocrystal Quantum Dots," *MRS Bulletin* 998-1004 (2001).

Pelton, M. et al. "Ultralow threshold laser using a single quantum dot and a microsphere cavity," *Physical Review A* 59(3):2418-2421 (1999).

Artemyev, M.V. et al. "Light trapped in a Photonic Dot: Microspheres Act as a Cavity for Quantum Dot Emission," *Appl. Phys. Lett.* 1(6):309-314 (2001).

Schacht, S. et al. "Oil-Water Interface Templating of Mesoporous Macroscale Structures," *Science* 273:768-771 (1996).

Huo, Q. et al. "Preparation of Hard Mesoporous Silica Spheres," *Chemistry of Materials* 9(1):14-17 (1997).

Yu, C. et al. "Synthesis of Siliceous Hollow Spheres with Ultra Large Mesopore Wall Sturcutres by Reverse Eulsion Templating," *The Chemical Society of Japan* 62-63 (2002).

Cha, J. N. et al. "Biomimetic synthesis of ordered silica structures mediated by block copolypeptides," *Nature* 403:289-292 (2000).

\* cited by examiner

FIG. 3
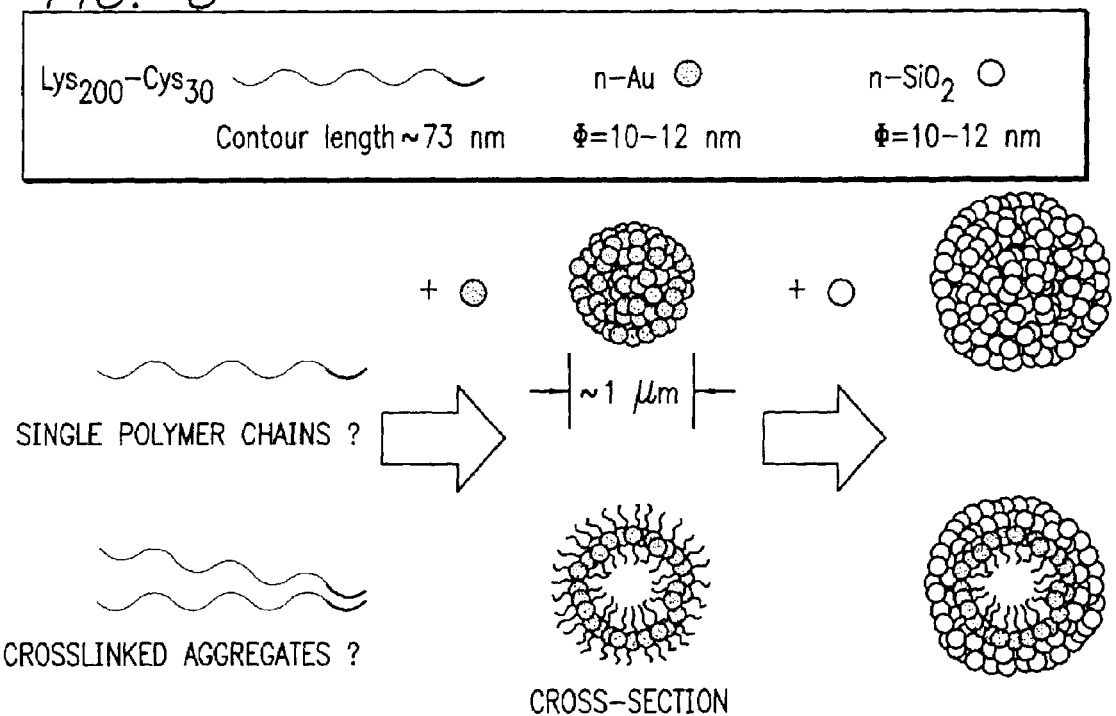
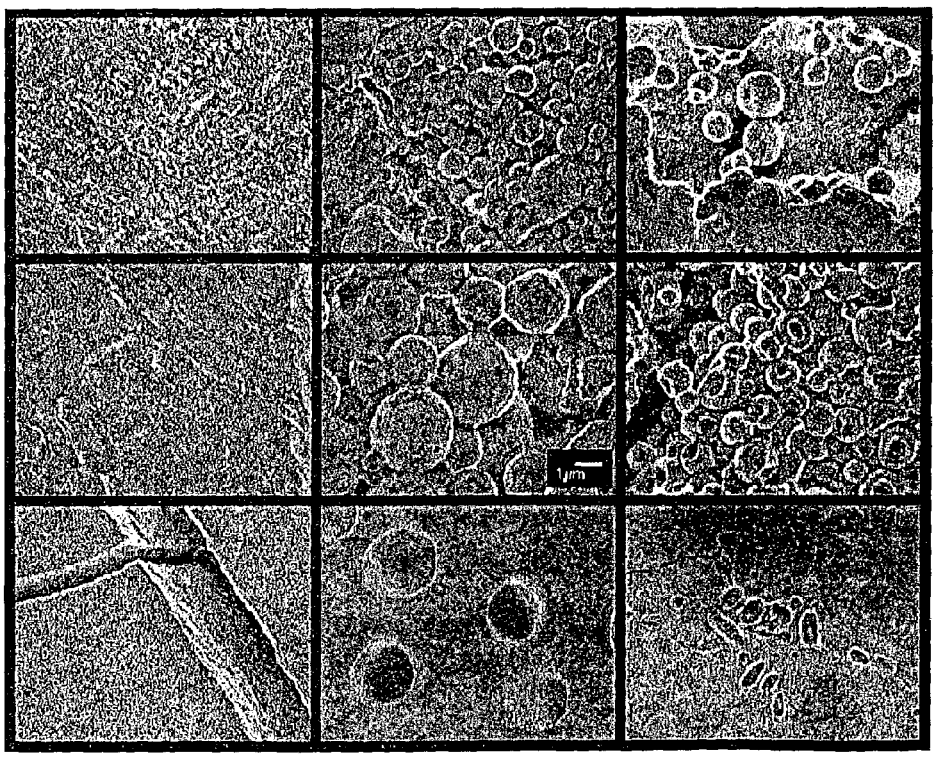
FIG. 4

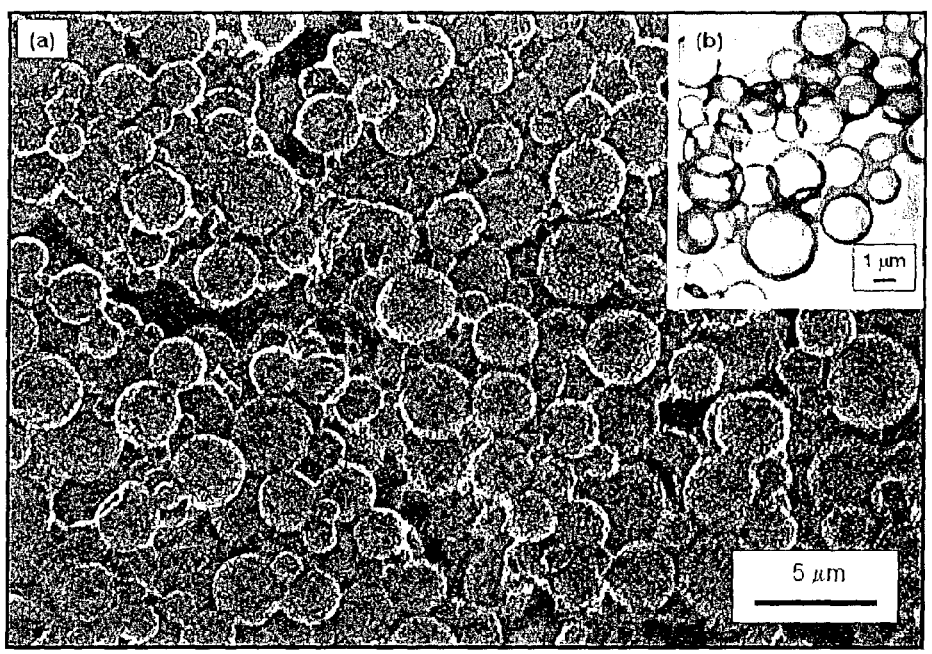
FIG. 8
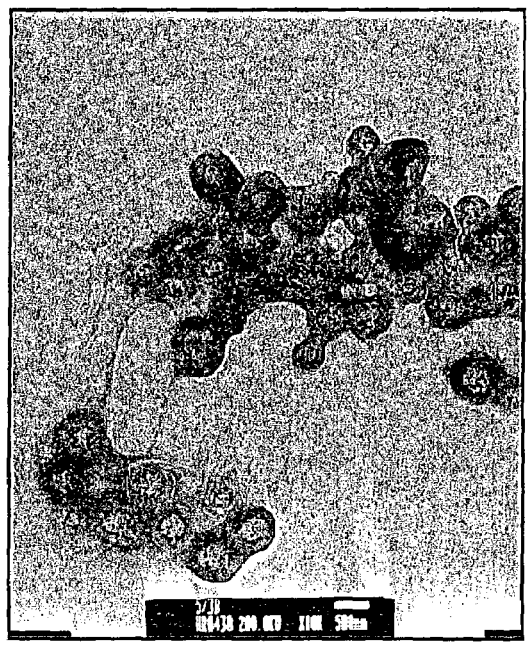 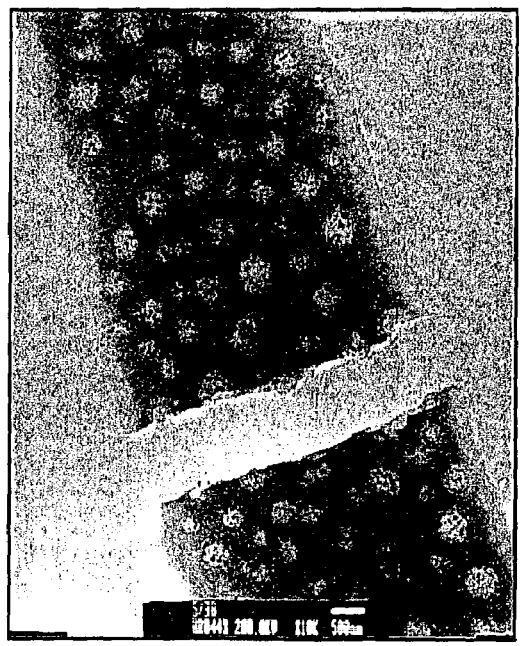
FIG. 9A          FIG. 9B

NANOPARTICLE ASSEMBLED HOLLOW SPHERES

RELATED APPLICATIONS

The present application claims the benefit of U.S. provisional application No. 60/326,870 filed Oct. 2, 2001 as well as U.S. provisional application No. 60/360,939, filed Mar. 1, 2002, both of which are incorporated herein by reference in their entirety.

STATEMENT REGARDING FEDERALLY SPONSORED RESEARCH OR DEVELOPMENT

This invention was made with Government support under Grant Nos. 0090034 and 9634396, awarded by the National Science Foundation. The Government has certain rights in this invention.

BACKGROUND

In a eukaryotic cell, genes are transcribed into messenger RNAs (mRNAs), and mRNAs are translated into proteins. When this process goes awry, cells may die or become cancerous. Upon disease onset, these catastrophic events are extremely hard to detect because of the clinician's inability to detect a single abhorrent cell or group of cells. Instead, disease is generally detected on the macroscale, resulting in large numbers of cancer cells that have to be surgically removed or killed by radiation or chemotherapeutic drugs. Moving from this macroscale therapeutic approach requires novel technologies, many of which are still being developed.

Although molecular therapy has made significant progress in the development of gene delivery systems that can change the genetic makeup of cells, and chemotherapeutic drugs have been engineered to be more specific in their effect on cell death, advances still need to be accomplished in all therapeutic systems that require the delivery of active biomolecules. Medical researchers continue to search for a reliable way to pinpoint drug delivery to specific cells, and many laboratories are relying on biochemical properties to help fabricate these therapeutic delivery systems. By targeting a specific cell surface characteristic, it may be possible to identify an individual cell population on the microscale instead of groups of cells or tissues on the macroscale. This targeting should provide an avenue for highly specific drug delivery. Encapsulation processes should increase half-lives of therapeutic agents and protect them from the immune-based degradation machinery that detects non-self contaminants. Delivery and encapsulation are intimately coupled because once the therapeutic agent has been encapsulated, delivery must occur for the action mechanism selected. Giving the therapeutic agent a way to be both encapsulated and possess its own address for delivery requires biological, chemical and physical design principles. Organic recognition elements (typically antibodies generated against a protein present on the target cell's surface or short peptides that also recognize cell surface proteins) have to be generated and attached to the surface to produce a biosignature, and genetic and drug therapeutic agents have to be physically incorporated into the delivery system.

The introduction of nanoparticles to this process provides at least three desired characteristics to a proposed delivery system, namely: 1) the correct length scale for biomolecular interactions, 2) physical support and 3) means of chemical attachment. Nanoparticles can be produced with very small diameters (<100 nm) and out of a variety of compositions, such as metals, metal oxides, metal non-oxides, and polymers, and they can be functionalized to behave as molecular linkers. Nanoparticles have physical, chemical and electronic properties uniquely different from those of single molecules and bulk materials. Because of their unique properties, there is a great research effort in trying to harness these properties to prepare medical devices utilizing nanoparticles. The synthesis of diverse nanoparticle species with different functional groups that allow needs-based designer modifications may be the next critical ingredient in gene therapy and imaging systems.

Significant progress has been made in the ability to deliver genetic therapeutics and chemotherapeutics to cells or groups of cells, but encapsulating the dual functions of payload and delivery have not been achieved. One of these techniques, liposome-mediated delivery, provides a therapeutic molecule with an encapsulating lipid bilayer. This method provides wide applicability to deliver different therapeutic molecules like proteins, peptides, and nucleic acids, making this delivery choice very attractive. Liposomal spheres are generated by mixing a drug-containing aqueous mixture with lipids, and creating spheres by nebulization or high speed vortexing resulting in both nanospheres and microspheres. The size of the sphere dictates the amount of therapeutic agent delivered. Researchers have created a size range of 5-500 micron uniform spherical droplets, and one research group has shown that the release rate depends on the size of the therapeutic-containing sphere[1]. This observation led to creating a nebulizer device that generates a range of sphere sizes simultaneously, providing time-released delivery of therapeutic agents, first from small spheres and then from large spheres[2]. However, severe obstacles faced are their lack of robustness[3], and the inherent difficulty of keeping lipid bilayers in micellar (spherical) form[4]. Other practical technical problems also plague this delivery system, namely:

1. The liposomal spheres have an extremely high polydispersity index, thus specificity is compromised at the first synthesis step.
2. It is hard to functionalize both the interior and exterior of liposomes.
3. There is a low therapeutic payload with respect to liposome size.
4. It has been difficult to target delivery to a specific cell type.

Liposomes circulate in the blood for long periods of time often evading detection by the body's immune system, enhancing the likelihood that the encapsulated drug will be delivered to its target, therefore mitigating harsh cytotoxicity coincident with many therapeutic treatments. In spite of these advantages, only three liposome-mediated drug delivery systems have overcome the barriers presented by the available methodologies and entered the drug market: doxorubicin, daunorubicin, and amphotericin B.

An alternative method for therapeutic delivery has been what some people refer to as nanomedicine[5]. An example of nanomedicine is nanoshells, hollow spheres made of silica nanoparticles and coated with gold nanoparticles[6]. Because of their extraordinarily small size (~10 nm), these spheres are embedded IN a matrix polymer and injected into the body[7]. It is thought that after heating with an infrared laser, the energy released from the nanoshells will make the polymer melt and release their drug payload at a specific site[6]. However, because they are on the nanoscale, it is hard to incorporate dual functionality into these nanoparticles themselves or produce them to be a self-delivery system; the polymer is required for encapsulation and thus obviates some of the benefits of producing nanosized molecules.

In contrast to silica nanospheres decorated with gold, bucky balls, carbon fullerenes, are also being tested as possible candidates for chemotherapeutic delivery[8]. Antibodies have been successfully attached to bucky balls[9], and bucky balls have also been decorated with antiviral agents[10]. However, several shortcomings compromise this drug delivery system:

1. Fullerenes are organic, thus not readily soluble in the aqueous phase where many biological interactions occur.
2. It is hard to disperse fullerenes in the blood because of poor mixing due to solubility.
3. The organic molecular environment in unfavorable to an antibody/antigen interaction, whereas the delivery system is dependent on this interaction occurring.
4. Functionalization of buckyballs occurs solely on the exterior, thus it is difficult to synthesize dual-function buckyballs, thereby restricting biochemical recognition.

The typical route chosen by chemists and materials scientists to assemble nanoparticles is to utilize and exploit specific biomolecular recognition, such as the complementarity of DNA nucleotides or enzyme substrate pairs[11], but dual-functionality is not accomplished. Gold nanoparticles have been bound to DNA TO form reversible aggregates[12], and gold particles have been successfully aggregated even in the shape of spheres approaching the microscale[13]. Dimers of cadmium selenide (CdSe) nanoparticles have been synthesized using bis(acyl hydrazide). Antigen-antibody interactions have also been utilized to assemble gold nanoparticles.[14] However, the use of DNA hybridization, protein substrate, or antibody/antigen interactions have not facilitated a single step, 'one-pot' synthesis of macroscopically phase-separated materials from nanoparticles, such as the hollow spheres presented in the present application.

Hollow spheres are an extremely attractive structural motif for many applications due to their encapsulation properties, and their preparation in the sub-micron diameter range has been an active area of materials chemistry[15]. In a typical procedure, large particles (submicron/micron diameters ~100's of nm) are coated with a ceramic (or polymer) precursor, and then the particle is removed to leave behind a ceramic (or polymer) shell. The size of the hollow sphere is controlled by the templating particle, the thickness of the shell is controlled by the deposition process, and the composition of the shell is determined by choice of precursor. Interesting variations include using gold nanoparticles to template polymer shells[16], and using polymer microspheres to template polyelectrolyte shells layer-by-layer and titania shells[17]. In a different approach, a polymer cast of an opaline structure of silica microspheres was created, the silica was removed and a ceramic precursor was deposited onto the interior polymer walls to construct titania hollow spheres[18]. While such preparation routes to hollow spheres appear quite flexible, they are a labor-intensive process, requiring multiple steps to be done in a sequential manner. Encapsulation of a desired compound within the hollow spheres is even more difficult to accomplish because the spheres can not be formed, dissociated (to allow agent incorporation) and reformed in physiological relevant synthesis conditions to protect from degradation of the desired compound which is usually a therapeutic agent.

SUMMARY

Nanoparticle three-dimensional composite structures such as inorganic vesicles or hollow spheres have until now been produced using either a layer-by-layer (LBL) assembly on sacrificial templates such as polystyrene or through surfactant stabilized oil-in-water emulsion droplets.[15-18] We present here an alternative, simple approach for the cooperative, single-step synthesis of nanoparticle vesicles and hollow spheres merely using the combination of nanoparticles and a structure-directing agent, such as block copolypeptide or homopolymer polyelectrolytes. Accordingly, compositions for use in the present inventions include a structure directing agent, wherein the structure-directing agent is a block copolypeptide or polyelectrolyte, and one or more types of nanoparticles having a binding affinity for at least a portion of the stucture-directing agent One embodiment of the present invention is a nanoparticle-containing microsphere comprising a structure directing agent, an inner layer comprising a first nanoparticle bound to a portion of the structure directing agent, and an outer layer coating the inner layer comprising a second nanoparticle bound to another portion of the structure-directing agent. Block copolypeptides for use in the present invention are designed so that one type of nanoparticle binds to one block of the block copolypeptide, whereas a second type of nanoparticle binds to a second block of the copolypeptide. Moreover, the C-terminus and/or N-terminus of the block co-polypeptide can be further modified with a functional group. Polyelectrolytes, such as poly-L-lysine or poly(allyaminehyrdochloride), can also direct self assembly of vesicular structures whenever a nanoparticle is bound to the polyelectrolyte by directional charge-stabilized hydrogen bonding. The nanoparticles are typically composed of metals, metal non-oxides, metal oxides and organics. Morever, interior nanoparticles may be functionalized to introduce therapeutic or imaging agents, whereas the nanoparticles on the exterior may be functionalized to introduce a recognition element for in vivo targeting.

The nanoparticle-containing microsphere may further comprise a payload encapsulated within the inner layer, such as drug molecules, therapeutic compounds, radioactive compounds, chemotherapy agents, nucleic acids, proteins, MRI contrast agents, preservatives, flavor compounds, smell compounds, colored dye molecules, fluorescent dye molecules, organometallic compounds, enzyme molecules, pesticides. fungicides and fertilizers.

Another embodiment of the present invention is a method of making a nanoparticle-containing microsphere. The first step of the method is combining a structure-directing agent and a first nanoparticle for a time and under conditions sufficient for the first nanoparticle to bind to a portion of the structure directing agent and self assemble into an inner shell. The next step is adding a second nanoparticle, of a different type than the first nanoparticle, under conditions sufficient for the second nanoparticle to bind to another portion of the structure-directing agent and for the second nanoparticle to form an outer shell coating the inner shell containing the first nanoparticle. The method can also include a calcination step to remove the structure-directing agent.

The invention described here makes use of nanoparticle design, nanobiotechnology and cooperative molecular self-assembly, all residing in the same process in order to provide encapsulation, with the dual functionality of both cell targeting and therapeutic delivery. Because a large number of primary functionalized nanoparticles are delivered to a targeted site by a single vesicle structure, there is a built-in site-specific amplification of the therapeutic agent; or in the case of magnetic imaging, an enhanced concentration of medical imaging agents at the desired cellular location.

Nanoparticles can be functionalized with chemical links that incorporate a variety of therapeutic agents, such as lipids, proteins, and nucleic acids, while still allowing their release. Additionally, they can be synthesized to possess a covalent link between the materials used for self-assembly and a recognition element.

Magnetic nanoparticles can also be used, thus providing a new route to real time imaging of cell recognition events. Packaging these different nanoparticles in microdelivery systems allows incorporation of biologically distinct biomolecules and magnetic particles. In addition, exterior silica nanoparticles can be functionalized with proteins that allow cellular recognition. Self-assembly occurs by virtue of ionic interactions to produce hollow microspheres with two types of functionalized nanoparticles, therapeutic agent bound particles on the interior, and protein-linked nanoparticles that recognize cell surface properties on the exterior (FIG. 1). This self-assembly allows targeted cellular delivery and release of payload, thus medical therapy and imaging occurs on the cellular level instead of the macroscale.

These and other features, aspects, and advantages of the present invention will become better understood with regard to the following detailed description and accompanying drawings.

BRIEF DESCRIPTION OF THE DRAWINGS

FIG. 3 is a schematic of the proposed mechanism of formation.

FIG. 4a-i are HRSEM images of n-Au/n-SiO$_2$/Lys$_{200}$Cys$_{30}$ prepared with various amounts of n-Au and n-SiO$_2$., magnification at 500 ×.

FIG. 8a-b is an HRSEM image (FIG. 4a) and a TEM image (FIG. 4b) of n-Au/n-SiO$_2$/Lys$_{200}$Cys$_{30}$ (as synthesized) showed on the same scale.

FIG. 9a-b are TEM images of n-Au/n-SiO$_2$/Lys$_{200}$Cys$_{30}$ as a network (FIG. 6a) and a film (FIG. 6b).

DETAILED DESCRIPTION

I. Overview

A design strategy for the supramolecular assembly of multi-compositional dual-functionality hollow microspheres starting from water-soluble nanoparticles and diblock copolypeptides or commercially available homopolymer polyelectrolytes has been developed. This highly processed synthesis is accomplished in a completely aqueous system and under ambient conditions of low pressure, room temperature and neutral pH. The molecular forces that drive the assembly and macroscopic phase separation are found to be a combination of electrostatic attractive forces, proton shuffling and directional charge-stabilized hydrogen bond formation[19]. Self-assembly in the presence of structure-directing polymers results in hollow spheres composed of an inner, thick, close packed array of gold, semiconductor or magnetic nanoparticles followed by an outer, thinner layer of silica nanoparticles (i.e. gold and silica assemblage, FIG. 1). In this micrograph, these chemically distinct nanoscaled regions are easy to visualize because of the differences in refractive indices, with electron dense gold nanoparticles in the interior, and optically clear silica nanoparticles on the exterior.

Figure 1:
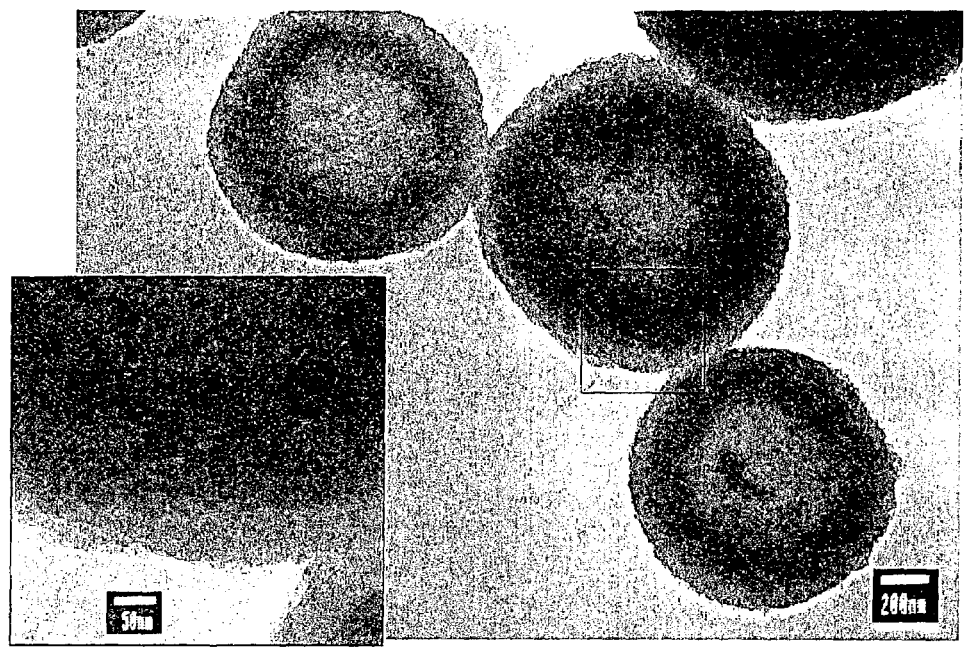
FIG. 1 is a TEM image of n-Au/n-SiO$_2$/Lys$_x$Cys$_y$, the inset image is a magnification of indicated region seen within the square.
Figure 2:
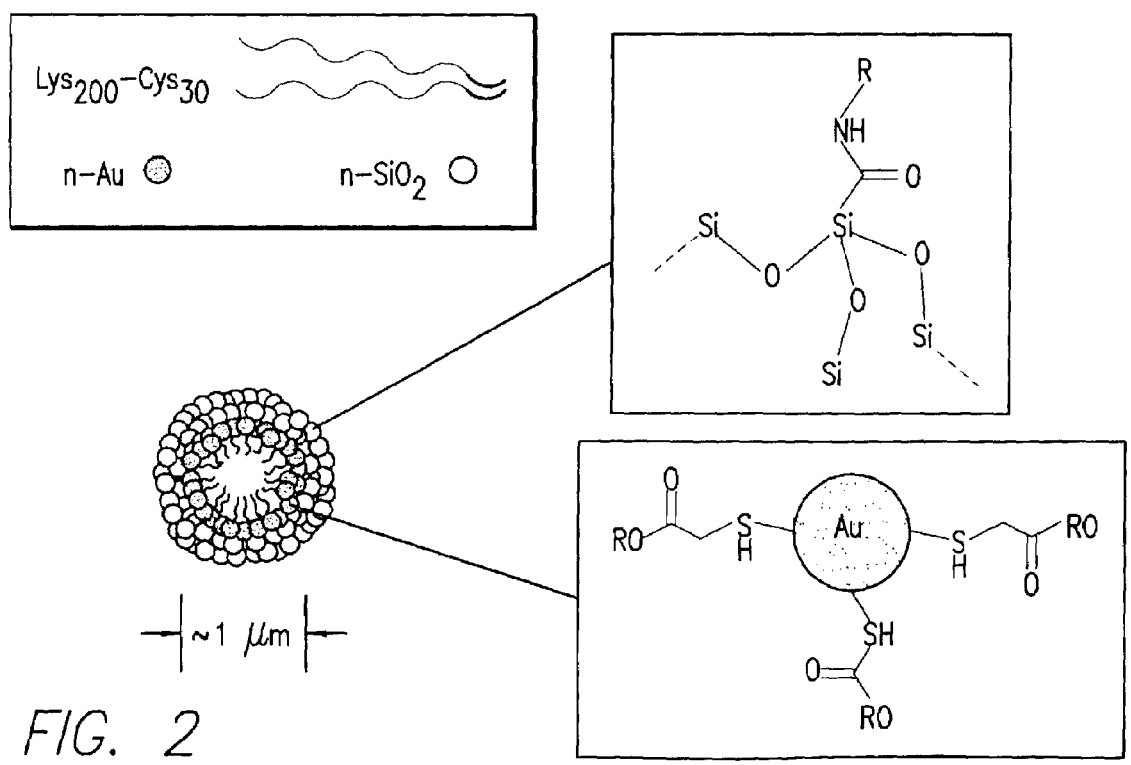
FIG. 2 shows Dual-Function Microspheres. where gold nanoparticles with a primary functionality are directed to interior of the hollow microsphere, and silica nanoparticles with a second functionality are directed to the exterior of the silica nanoparticle shell.

Bicompartmentalization of the hollow microspheres by this phase separation provide a means for encapsulation and multifunctionality not previously possible. These microspheres have mechanical strength and porosity because of the silica nanoparticle arrangement and packing on the exterior. The porosity of the microspheres is a necessary feature to allow solute exchange, thus providing a stable environment for, and increasing the half-lives of, the therapeutic contents. Additionally, the use of diblock copolypeptides or homopolymer polyelectrolytes as the organic templates structurally direct the synthesis so that they are pH and salt responsive. This responsiveness can be used to enable the rapid disassembly of the hollow spheres in vivo with the release of the primary functionalized particles that are on the interior of the sphere for therapeutic agent delivery at sites specifically determined by the secondeary functionalization of the silica particles on the exterior of the hollow sphere (FIG. 1).

II. Composition

Compositions for use in making nanoparticle-containing microstructures, such as vesicles, hollow microspheres, "apples," "cups," and films generally include a structure directing agent and one or more types of nanoparticles A. Nanoparticles Nanoparticles for use in the present invention can be composed of metals, metal non-oxides, metal oxides, or organics. Metal nanoparticles can include gold, silver, platinum, palladium, copper, rhodium, rhenium, nickel, and iridium; alloys of metal nanoparticles, such as platinum and iridium. Metal non-oxide nanoparticles include II-VI, III-V, and IV quantum dots; and metal oxide nanoparticles can include titanium oxide, zirconium oxide, aluminum oxide, iron oxide, tungsten oxide, cerium oxide, antimony oxide and silicon oxide. Examples of hydrophobic nanoparticles include polystyrene and polypyrrole. Moreover the nanoparticles can be functionalized with molecules to provide a positive or negative charge. Alternatively, the nanoparticles can be functionalized with molecules to provide a hydrophobic or hydrophilic surface. Typically, the nanoparticles will have diameters of 1-100 nm, and may include shapes other than spheres, such as rods, triangles, and hexagons.

It is noted that the nanoparticles can be prepared in-house or acquired from commercial sources. Examples of negatively charged nanoparticles suitable for use in the present invention include silica, citrate coated gold, citrate stabilized CdSe quantum dots, and tungsten oxide. An example of a positiveley charged nanaoparticle is titanium oxide.

B. Stucture-Directing Agents

Sturcture directing agents suitable for use in the present invention generally comprise a polymer in which at least one portion of the polymer has a binding affinity for one or more nanoparticles. Preferably the structure-directing agent is a synthetic biopolymer having a binding affinity for two or more different nanoparticles.

The cooperative three-dimensional assembly of nanoparticles into hollow microspheres can be accomplished using block copolypeptides, polypeptide-random coil block co-polymers (such as polyethylene oxide, polyethyleneglycol, polyamines or other water soluble polymers), or commercially available homopolymer polyelectrolytes (e.g. polyamines) in a completely aqueous, room temperature process under mild pH conditions. This 'one-pot' self-assembly process occurs rapidly (less than one minute).

Block copolypeptides or homopolymers with specific binding affinities to metals, metal chalcogenides, metal oxides, or organics can be prepared via stepwise living polymerization of the appropriate amino acid N-carboxyanhydride monomer precursors using 2,2'-bipyridylnickel(1,5-cyclooctadiene) metal initiator invented by Deming [Deming, 1997]. The blocks of the copolypeptides or homopolymers are derived from the 20 natural amino acids (lysine, arginine, histidine, aspartic acid, glutamic acid, glycine, alanine, valine, leucine, isoleucine, methionine, proline, phenylalanine, tryptophan, serine, threonine, asparagine, glutamine, tyrosine, and cysteine).

In one version of the present invention, nanoparticles arrange to form hollow spheres and other complex microstiructures using carefully designed block copolypeptides as the structure-directing agent. Previously, these block copolypeptides were found to produce silica micron-size spheres and columns from tetraethylorthosilicate (TEOS) at pH 7 and at room temperature [Cha et al., 2000]. The method of the present invention eliminates the complex reactions of hydrolysis and condensation when using TEOS, and focuses on the directed assembly properties of these block copolypeptides.

In general, a diblock copolypeptide is designed with the ability to bind to two different types of nanoparticles. For example, copolypeptides with positively-charged peptide blocks of lysine, arginine, or histidine, will have binding affinities for silica and other negative-charged nanoparticles Conversely, copolypeptides with negatively-charged peptide blocks of as aspartic acid and glutamic acid will have binding affinities for nanoparticles that are positively-charged. Copolypeptides can also include nonpolar peptide blocks comprised of amino acids that can associate with nanoparticles through hydrophobic interactions, such as, glycine, alanine, valine, leucine, isoleucine, methionine, proline, phenylalanine, and tryptophan. Moreover, copolypeptides can also include uncharged, polar peptide blocks of amino acids that can associate with nanoparticles through hydrophobic and hydrogen-bonding interactions, such as serine, threonine, asparagine, glutamine, tyrosine, and cysteine. In addition, copolypeptides can include peptide blocks that can covalently bond to nanoparticles or to nanoparticles functionalized with receptor-like molecules. Alternative versions can include copolypeptides functionalized at the C terminus and/or N-terminus with a functional group e.g., organic molecules, organic fluorophores, or biomolecules, before formation of the encapsulating nanoparticle shell.

The peptide blocks of the copolymers can be homopolymers or a random peptide block sequences having a defined composition of two or more amino acid monomers. Typically, blocks of the copolypeptides will have lengths of 10-400 residues. Moreover, the structure-directing agents can include copolypeptides having more than 2 blocks or a combinations of copolypeptides.

In a preferred version of the present invention the block copolypeptide is a poly (L-lysine$_{200}$-b-L-cysteine$_{30}$) polymer produced by a stepwise living polymerization using N-carboxyanhydride monomeric amino acids and 2,2-bipyridylnickel (1,5-cyclooctadiene) metal initiator in THF.[20] After polymerization, the copolypeptides are deprotected and dissolved in water. The resulting three dimensional structure of the copolypeptides has not been solved, but disulphide bridges form between the cysteine residues causing these residues to make a hydrophobic core, allowing the hydrophilic lysine residues (pKa=9) to interact with negatively charged species in the aqueous phase. An added feature of these diblock copolypeptides is that the sulfur atoms in the cysteine residues will bind tightly to metals like gold.

In another version of the present invention the structure directing agent/polymer is a polyelectrolyte, such as the polyamines poly-L-lysine 100-300 or poly(allylamine hydrochloride). These homopolymers unexpectedly exhibit the ability to bind two different types of nanoparticles and drive the self assembly of hollow spheres through a combination of electrostatic attractive forces, proton shuffling and directional charge-stabilized hydrogen bond formation. In particular, the transition in the interfacial molecular forces from pure electrostatic charge-charge interactions to one of directional charge-stbilized hydrogen bonding driving self assembly is primarily dependent on the differences in pKa values between proton donors and acceptors. Accordingly, preferred versions of polyelectrolytes serving as structure-directing agents will contain functional groups having a pKa less than about 6 pKa units, and preferably less than about 4 pKa units, than the pKa value of a corresponding functional group of the nanoparticle.

C. Microstructures

The compositions of the present invention form unusual microstructures, such that nanoparticles of one composition are spatially oriented completely interior or exterior to nanopartricles of a second composition. They form sub-micron/micron sized aggregates, typically about 500 nm to about 5 μm in diameter, having unusual morphologies, such as spheres, "apples" and "cups." These shapes can also be fabricated into films.

One version of the present invention is a nanoparticle-containing vesicle, comprising a structure directing agent; and a first nanoparticle bound to the structure-directing agent. The composition self assembles into a vesicle, which may serve as a precursor forming the interior shell of hybrid microspheres.

Another version of the present invention is a nanoparticle-containing microsphere comprising a structure directing agent, an inner layer comprising a first nanoparticle bound to a portion of the structure directing agent, and an outer layer coating the inner layer comprising second nanoparticle bound to another portion of the structure-directing agent. These microstructures are hollow sub-micron/micron-sized organic-inorganic spheres, in which an outer shell comprising the second type of nanoparticle encapsulates an inner shell comprising the first type of nanoparticles.

When the nanoparticle-containing microspheres are calcined, they remain hollow and intact, as determined from TEM and SEM. Accordingly, yet another version of the present invention is a hollow microsphere comprising an inner shell comprising a first type of nanoparticle; and outer shell comprising a second type of nanoparticle coating the inner shell, devoid of the organic components removed by calcination.

If the organic components are not removed from the hybrid spheres, other organics may be introduced by functionalization of either (or both) termini of the copolypeptide with organic molecules, organic fluorophores, or biomolecules before the formation of the encapsulating nanoparticle shell. Alternatively, the nanoparticles themselves may be functionalized.

Preferred versions of the microspheres include an inner layer containing semiconductor nanocrystals, gold, silver, or magnetic nanoparticles, and nanoparticles functionalized to introduce therapeutic agents for release, e.g., lipids, proteins, nucleic acids, or imaging agents. Moreover, preferred versions of the outer layer contain silica nanoparticles, CdSe quantum dots (QD) functionalized with mercaptosulfonic acid, or nanoparticles functionalized to introduce a recognition element for in vivo targeting.

One objective of this invention is to produce nanoparticle-containing microdevices for therapeutic agent delivery, sensing and real-time medical imaging. In this new approach multi-compositional hollow multilayer organic/inorganic vesicles are used as functionalized nanoparticle vehicles. One set of nanoparticles, which makes up the exterior part of the vesicle, is functionalized (called secondary functionalization) for the in vivo targeting by the vesicle of a specific cellular address. The interior of these multi-layer, vesicles is made up of a second set of nanoparticles, which are functionalized (called primary functionalization) with therapeutic agents that are to be released at a specific cellular address. The second set of nanoparticles may also have a composition that meets the requirements needed for site selective medical imaging.

Another version of the present invention is a nanoparticle-containing microsphere, further comprising a payload encapsulated within the inner layer. For medical applications the payload to be delivered can include drugs, therapeutic compounds, radioactive compounds, chemotherapy agents, DNA or RNA, proteins, and MRI contrast agents. For consumer food products or cosmetic applications the payload could include preservatives, flavor or smell compounds and colored dye molecules. Encapsulation of the payload within the interior of the hollow spheres can be performed using a solute dissolved in liquid media, such as the aqueous synthesis medium or other solute-containing solvent or encapsulation of a sol, such as a ferrofluid, within the interior of the hollow spheres.

III. Method of Making

The present invention includes methods for making nanoparticle-containing microstuctures having morphologies, such as vesicles, spheres, "apples", and "cups," which are typically conducted under ambient conditions, i.e., low (atmospheric) pressure, room temperature and neutral pH One embodiment of the present invention is a method of making a nanoparticle-containing vesicle by combining a structure-directing agent and a first nanoparticle for a time and under conditions sufficient for the nanoparticle to bind to a portion of the structure directing agent and self assemble into a vesicle.

Another embodiment is a method of making a nanoparticle-containing microsphere, which includes the additional step of adding a second nanoparticle, of a different type than the first nanoparticle, under conditions sufficient for the second nanoparticle to bind to another portion of the structure-directing agent and for the second nanoparticle to form an outer layer coating an inner layer of the vesicle containing the first nanoparticle. Yet another embodiment includes a calcination step to remove the stucture-directing agent.

In a preferred embodiment using a block copolypeptide as the structure-directing agent, the synthesis reaction can be performed at room temperature. As shown schematically in FIG. 3, a solution of a particular nanoparticle is added to the block copolypeptide solution, at which point the nanoparticles bind to one of the blocks of the copolypeptide. A second solution of another type of nanoparticle is then added to the same solution, at which point these nanoparticles bind to the other block of the copolypeptide. The resulting product is micron-sized organic-inorganic spheres, in which a thick shell comprising the second type of nanoparticle encapsulates a thin shell comprising the first type of nanoparticle with an organic filler (i.e. the diblock copolypeptide) (see FIG. 1).

As an example, a $Lys_{200}Cys_{30}$ (g/mol=28,890) solution was prepared with a working concentration of 2.5 mg/ml (86.5 $\mu$M), and added to a 1.5 ml microcentrifuge tube with 125 $\mu$l of a citrate solution containing gold (Au) nanoparticles (9.4 $\mu$mol-particle/L). The Au solution color changed from ruby red to violet purple after addition, indicating that the Au particles aggregated, thus causing a red shift in the plasmon resonance frequency. Using a JEOL2010HR microscope equipped with a $LaB_6$ gun and operated at an accelerating voltage of 200 kV, a transmission electron microscope (TEM) image was obtained of the Au nanoparticle/polymer showed large (~1 $\mu$m), discrete regions of Au nanoparticles (FIG. 1). After ~5 minutes of aging with occasional agitation, 125 $\mu$l of a solution containing $SiO_2$ nanoparticles (~10-12 nm, Nissan Chemicals, Tokyo, Japan) (360.1 $\mu$mol-particle/L) was added to the Au nanoparticle/polymer mixture, $SiO_2$ nanoparticle clustering occurred causing the clear, purplish solution to become turbid. After agitating for a few seconds and sitting for 15 minutes, the purplish color began to settle to the vial bottom. After 24 hours, purple flocculent was found at the vial bottom. This precipitate was composed of hollow microspheres (see FIG. 1). In order to determine if conditions had been optimized for microsphere synthesis, reactions were done where titrations of the separate nanoparticles were added to the reaction (FIG. 4). The samples were examined via SEM 12 days after their preparation, and SEM images clearly show that equal starting concentrations of nanoparticles produced microspheres whereas varying the concentration of either type of nanoparticle caused loss of microsphere formation.

In an example of another preferred embodiment, nanoparticle vesicles were spontaneously and hierarchically assembled from simple polyamine polyelectrolytes and water-soluble, negatively charged inorganic nanoparticles. Addition of silica nanoparticles to the vesicles generated stable micron-sized hollow spheres, the walls of which were formed of a thick, inner layer of close-packed semiconductor nanocrystals surrounded by an outer layer of silica. The assembly of the nanoparticle vesicles as well as of the hollow spheres is in direct contrast to the typical methods employed that use either tailored block copolymers or sacrificial and oil-in-water emulsion templating to produce such structures.

The chemical interaction driving the macroscopic phase separation in this completely aqueous system is proposed to be one of charge-stabilized hydrogen bonding between the positively charged amines of the homopolymer polyelectrolyte poly-L-lysine and the negatively charged, oriented citrate molecules stabilizing inorganic nanoparticles. The ease and processibility of the synthesis gives promise to a diverse array of materials ranging in applications from drug delivery to catalysis to micron-scale optical devices.

Figure 5A:
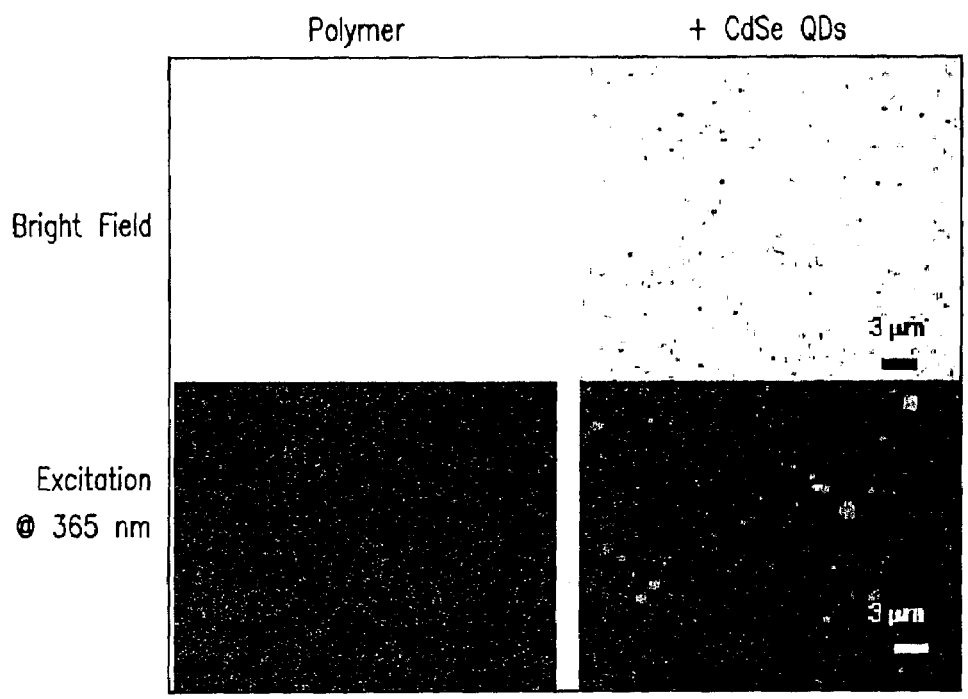
FIG. 5(A) shows bright field and fluorescence optical microscopy images of polymer solutions before and after the addition of citrate stabilized CdS/CdSe core-shell quantum dots and. (B) shows Autocorrelation functions of the nanoparticle vesicles in water at different scattering angles: 40° (filled squares), 70° (open circles) and 100° (filled triangles).
Figure 5B:
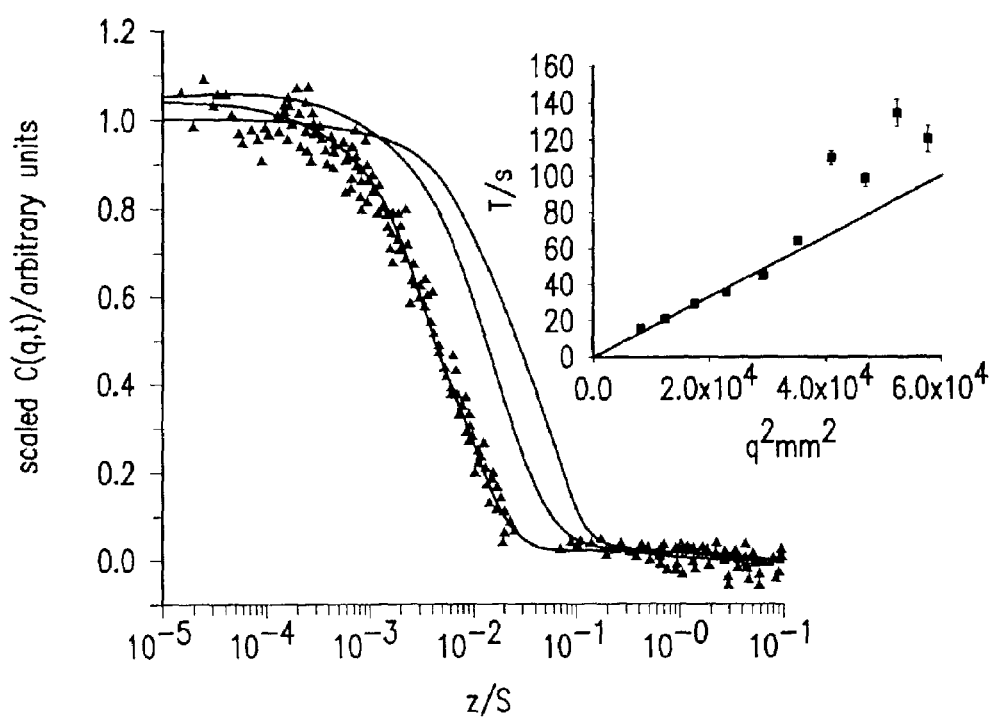
Figure 6:
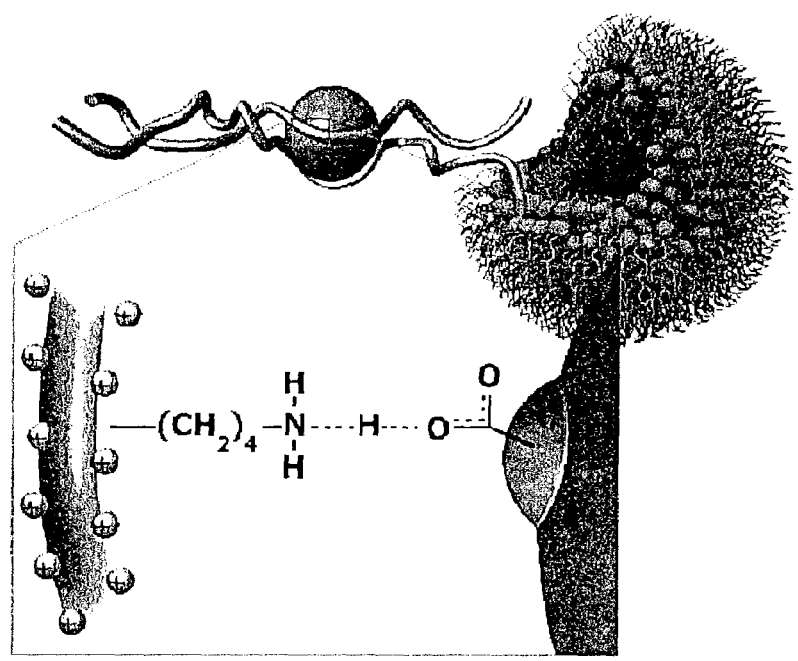
FIG. 6 is a schematic diagram of the nanoparticle vesicles and the directional charge stabilized hydrogen bonds that form between the amines of the poly-L-lysine and the carboxylic acid group (pK$_3$) of the citrate stabilized quantum dots.

Based on the visible and microscopic observations, pH titration and salt gradient experiments, a model can be proposed for the interfacial molecular forces that drive the macroscopic phase separation and formation of the poly-L-lysine nanoparticle vesicles. When the negatively charged citrate stabilized quantum dots are first introduced into the poly-L- lysine solutions, the transparent polymer solutions become turbid, indicating aggregation due to long-range Coulombic attractive forces and charge matching. The initial cloudy solutions then visually undergo a phase change to an "oil in water" like emulsion (FIG. 5) and it is proposed that this is due to a transition in the interfacial molecular forces from pure electrostatic charge-charge interactions to one of directional charge-stabilized hydrogen bonding (FIG. 6). Charged hydrogen bonds and proton shuffling have been shown to play key roles in biological activities such as enzyme catalysis and are primarily dependent on the differences of pKa values between the donor and acceptor molecules.[34-35] Hydrogen bonds are expected to be strongest when the difference in pKa between the donor and acceptor is small and it has even been determined that in pKa matched systems, the hydrogen bonds have covalent characteristics.[36] The substantial difference of six pKa units between the primary amine of poly-L-arginine and the carboxylic acid group of citric acid may explain why polyallylamine (pKa ~10.5) and poly-L-lysine, which have a difference of only approximately four pKa units, could successfully assemble the citrate-stabilized nanoparticles into vesicles, but poly-L-arginine could not. The large difference between the pKa of poly-L-arginine and the $pK_3$ of citric acid would thus most likely cause the interactions between the molecular ligands to remain essentially direct ion-pair electrostatic with only very weak hydrogen bonding.

We propose that the combination of electrostatic affinities and charged hydrogen bonding between the poly-L-lysine and the citric acid functionalized quantum dots creates a zone around each nanoparticle that is more neutral and less hydrophilic as compared to the immediate region associated with the excess polyamine. As stated earlier, an excess of the number of positive charges associated with the polymer relative to the number of carboxylic acid groups ($pK_3$) is required for these vesicles to form and it is therefore safe to assume that the initial negatively charged $pK_3$ carboxylic acid group of the citrate-coated nanoparticles become completely neutralized after reaction with the polypeptide. These uncharged nanoparticle amine units in essence then become what is typically the lipid layer of a conventional organic vesicle and the excess poly-L-lysine chains that are not interacting with any nanoparticle become what are usually the polar head groups (FIG. 6)

As noted above, one of the predominant molecular forces in biological systems is intermolecular, charge-stabilized hydrogen bonding, where the strength of these interactions is dependent on the relative pKa values of the donor and acceptor groups. The most widely studied example that uses such Lewis acid base chemistry is the proteolytic enzyme, where proton shuffling in the active sites provides the necessary driving forces for biocatalysis. The model that we propose here is an adaptation of this non-covalent chemistry for the supramolecular assembly of semiconductor nanocrystallites into vesicles starting from completely charged species. While one of the more common bio-inspired techniques for producing nanoparticle superstructures has been to use highly specific molecular recognition events, such as receptor ligand associations, we have demonstrated an alternative, more general, and possibly versatile approach for the multicompositional, 3-d cooperative assembly of organic and inorganic species into spatially defined domains: to simply use the very same Lewis acid base chemistry and proton shuffling that is seen throughout all of enzyme catalysis.

IV. Method of Using

This invention relates to a facile preparative system for the highly selective delivery of organic and inorganic molecules providing drug delivery, gene delivery, sensing and medical imaging. The preparative system provides a synthesis route using multi-compositional, multi-functional organized nanoparticles in a multi-compositional hollow sphere creating microdevices for therapeutic agent delivery, sensing, and real-time medical imaging. Use of these microdevices is not limited to, but includes nanomedical science, sensing, imaging, and real-time imaging both in vivo and as a process stream (i.e. factory production). The high range of functionalities that have been introduced into this network provides a diverse platform for the targeted reagents, thus lowering the costs of therapeutics thereby lowering cost and increasing the efficacy of treatment.

These robust materials are anticipated to have great promise in applications that require surface catalysis, magnetic/electronic/optic properties, transport capabilities, and combinations thereof, such as drug delivery, packaging, catalysis, and sensors.

For example, the nanoparticle-containing microstructures of the present invention may be used for medical applications, wherein the cargo to be delivered can be drug molecule(s), therapeutic compound(s), radioactive compound(s), chemotherapy agent(s), DNA/RNA, proteins, or MRI contrast agents. The mode of delivery can include aerosol delivery to lungs via inhalation, subcutaneous injection, ingestion, transdermal delivery (as ointment), and targeted delivery (via attachment of organ-specific molecules to the shell exterior).

For applications in catalysis, catalytically active sites can be located inside the hollow spheres. Examples include metallic nanoparticles on the inner walls, organometallic compounds bound on the inner wall, organometallic compounds dissolved in a fluid inside the hollow sphere or enzyme molecules dissolved in a fluid inside the hollow sphere. Catalysis applications can include partial oxidation reactions, oxidation reactions (to destroy organic pollutants in the air or water), biocatalysis (using enzymes-containing hollow spheres as bioreactors), enantioselective catalysis (to produce precursors to drug molecules), on-demand catalysis, and organic reactions catalyzed by metals The nanoparticle-containing microstructures of the present invention may also find applications as ceramics, e.g., coatings as a thin film of hollow spheres or dielectric material for electronics. In addition they may be used as a component in dispersions, such as paints, sun tan lotion, and perfumes. Agricultural applications would include the encapsulation and slow release of pesticide, fungicide, or fertilizer. For consumer food products the cargo to be encapsulated (and slowly released, if needed) can include preservatives, "flavor" compounds, "smell" compounds, and colored dye molecules. Further applications may include sensor devices containing encapsulated fluorescent dye molecules or as a chemical sensor/detector, wherein a dye molecule would change colors if it comes in contact with a chemical compound to be detected In order to demonstrate the multi-functionality of this microsphere assembly process and to validate the quality of the three-dimensional multiple length scale, multi-component assembly process; semiconductor nanoparticles were used instead of gold as a means of optically tagging the microspheres. If the nanoparticle assembly described above is valid, one should be able to observe the simultaneous effects:

1. Quantized electron confinement on the nanoscale within the semiconductor array on the interior of the microsphere
2. Confinement of the emitted photons on the micron length scale within the microsphere cavity (e.g. microcavity lasing).

Semiconductor nanocrystals have been demonstrated to have significant potential as inorganic chromophores ranging from biological tagging to photovoltaics and lasing.[11,21,22] Bawendi, Klimov and co-workers previously demonstrated that for stimulated CdSe QD emission to occur, a high QD volume fraction and fast optical pumping are prerequisites for overcoming the non-radiative decay processes dominated by Auger recombination.[23] In addition, a major requirement for lasing is that the spontaneously emitted photons are coupled to an optical feedback medium in order to undergo stimulation. Spherical microcavities represent the ideal feedback geometry for confining the propagation of light in three dimensions and thus are ideal for optical nanoscale devices.[24] To date, glass and polymer spheres have successfully been used as substrate microcavities to modify the spontaneous emission of cadmium selenide (CdSe) quantum dots (QDs).[25-26] Recently, lasing from CdSe QDs and quantum rods have also been reported where substrate cavities such as glass and polymer microspheres, distributed feedback gratings and microcylinders were used as optical feedback media.[22,23,26]

In this miscrosphere self-assembly method, the light emitted by the CdSe QDs is not coupled to that of a separate substrate resonator but rather is trapped in its own self-assembled three-dimensional CdSe spherical microcavity. Using the method above with CdSe nanoparticles, hollow semiconductor microspheres were cooperatively assembled with walls composed of a thick (~200 nm), close-packed inner layer of core-shell CdS/CdSe quantum dots surrounded by an outer thinner layer (~70 nm) of silica nanoparticles. The quantum dot dimensions as determined by TEM and optical absorption, were found to be 28 Å and 40 Å (HOMO LUMO gap energy of 2.4 and 2.2 eV, respectively) and showed a narrow size distribution. These quantum dots were overcoating with CdS because when non-overcoated CdSe nanoparticles were used instead for microsphere synthesis, the nanocrystal luminescence was substantially quenched, indicating further that strong surface interactions are occurring between the individual CdSe nanoparticles in the synthesized microcavities.

The macroscopic and spectroscopic properties of the individual microcavities were characterized using a laser-excitation photoluminescence (PL) microscope set-up. All measured samples were prepared on thin quartz slides by air-drying, and prior to all spectroscopic analyses the geometrical and optical properties of the individual spheres were investigated; the PL images were obtained by excitation with the 365 nm line of a continuous wave argon ion laser.

Figure 7:
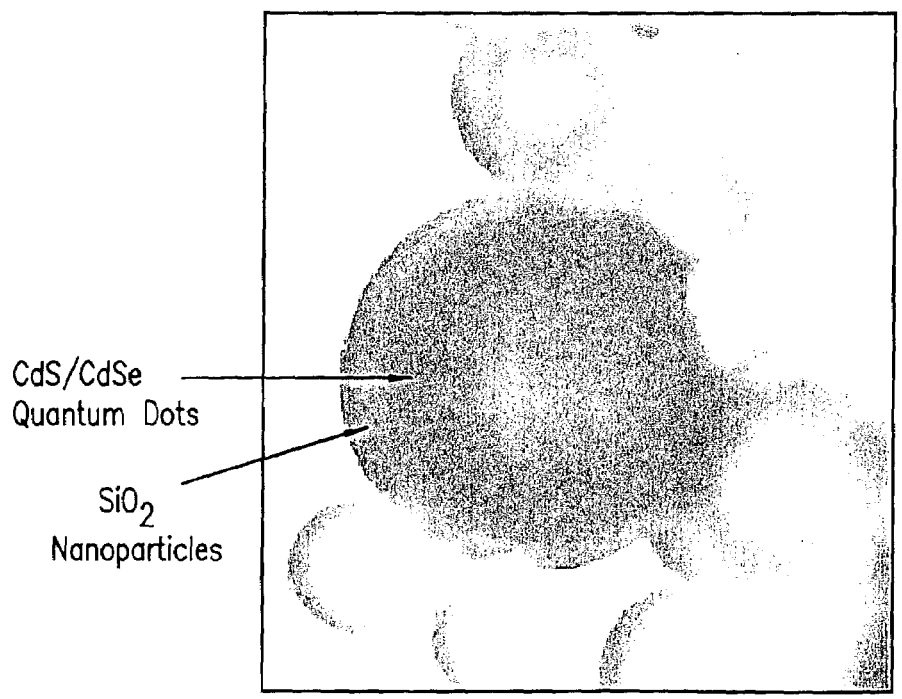
FIG. 7 shows a.transmission electron micrograph of a self-assembled hollow sphere where the cavity wall is composed of a close-packed inner layer of core-shell CdS/CdSe citrate stabilized quantum dots surrounded by a distinct outer layer of silica nanoparticles.

A representative TEM image of one such hollow double-layer silica/CdSe microsphere with a diameter of 3.7 µm is shown in FIG. 7. In general, all of the microspheres investigated for their optical properties were uniformly round in shape and demonstrated smooth surfaces. FIG. 5 shows two images comparing a phase contrast image and the resulting green luminescence image of the of the same spheres after laser excitation of the CdSe QDs (28 Å in diameter). This demonstration of self-assembled CdSe/CdS microcavities provides a clear example of optical confinement of a quantum-confined material, by coupling the electronic states of the three-dimensional confined semiconductor nanoparticles to the photonic states of the spherical microcavity.

In summary, the validity of the revolutionary new approach for nanoparticle packaging has been demonstrated. The specific cooperation between the inorganic nanoparticles and the polymer chains induces a phase transition from a uniform aqueous system to a water emulsion created by the formation of citrate-lysine ion pair interactions, which provides the basis for the hollow sphere assembly. The predominantly electrostatic interactions at the organic/inorganic interface also fulfill the requirement of high QD fill factors. Furthermore, the ability to synthesize a close-packed QD resonator enables both stimulated emission and QD lasing to occur. These self-assembled hollow microspheres provide a new concept for microcavity lasing, where the symbiotic interaction of the mode properties of the cavity with its emitting building blocks results in single mode lasing without using any additional artificial means, such as mirrors, gratings or spheres. Additionally, because of the high quality and narrow polydispersity of these miccrospheres, we have detected whispering gallery modes confirming photonic confinement.[27] This demonstration of confining electronic environments coupled with signal detection may have a profound impact on targeted delivery to a distinct cell population coupled to electronic detection, and also confirms the high degree of control that we can use to assemble multicompositional nanoparticle arrays for therapeutic applications.

V. Advantages

The advantages and improvements of the present invention over existing techniques and features are: extreme simplicity and ease of preparation of new approach; low-temperature, single-step synthesis; extremely general method to produce organic-inorganic hybrid materials; different structures of hybrid materials are achievable; hybrid materials have desirable encapsulation properties; and organics from hybrid spheres can be removed easily to produce hollow spheres. Larger structured materials can be assembled with the hybrid or hollow spheres of the present invention. Potential applications of these "nanocapsules" include drug delivery, chemical storage, contaminated waste removal, gene therapy, catalysis, cosmetics, magnetic contrast agents (for use in magnetic resonance imaging), and magnetooptoelectronics. Porous films produced with our method can find use as low-k dielectric materials, insulation, catalysts and separation membranes.

The ability to self-assemble biomolecules provides a synthesis route for drug delivery systems that have not been previously possible. The advantages of this self-assembly system are:

1. The use of biofriendly materials for the self-assembly process.
2. Delivery vehicle is stable in an aqueous environment, thus more biocompatible.
3. The use and ability to selectively assembly 3-dimensional arrays of different nanoparticle materials for functionalization in spatially distinct regions.
4. Producing functionalized nanoparticles that attach to nucleic acids for genetic therapy delivery systems.
5. Producing magnetic nanoparticles for real-time imaging.
6. Producing functionalized nanoparticles with proteins that recognize specific cell surface molecules.
7. The packaging of these nanoparticles so that two different functions are represented on a single microsphere, one on the interior and one on the exterior.
8. The ability to disrupt the sphere ionically by both pH and salt gradients for payload delivery.

VI. Additional Embodiments

The compositions and methods of the present invention can be extended to a global technique that includes nanoparticle functionalization and attachment of molecules to produce a novel delivery system based on biocompatibility, and both nanoparticle and microsphere design by functionalization of said components in the microdevice, including, but not excluding, copolymers, diblock copolypeptides, polymers, metallic nanoparticles, metal oxide nanoparticles, polymer nanoparticles and functionalization chemical processes. The results of this design strategy results in a multi-functional, multi-utility device whose function allows a delivery process in such areas as therapeutic agent delivery, chemotherapeutic agent delivery, sensing and imaging. Accordingly the present invention includes the ability to functionalize nanoparticles to allow localization, delivery, and payloading of agent. It should be apparent to those skilled in this art that it does not exclude the delivery of non-bioactive species but may include inorganic species such as photoconductors and contrasting agents (like cesium bromide) for imaging.

Our methodology should be extremely amenable to variations, as listed in the following;
1. Use of any diblock copolypeptide to modify characteristics of microsphere on both micro and nano-scales.
2. Use of any charged homopolypeptide
3. Use of any non-amino acid based polyelectrolyte—negatively charged, positively charged, amines, carboxylic acids
4. Use of water-soluble nanoparticles with different stabilizing ligands
5. Use of nanoparticles of other compositions, including, metals, other II-VI semiconductor, III-V semiconductor, magnetic, polymeric, transition metal oxides.
6. Functionalization of nanoparticles for molecular attachment
7. Biosignature-based delivery system
8. Increased payload capacity of therapeutic agent, sensing molecule or imaging molecule.
9. A design strategy that allows increased functionality of the microsphere by assembling chemical moieties for needs-based properties.

EXAMPLES

Example 1

Au/SiO$_2$ Hybrid Spheres Using Lys$_{200}$Cys$_{30}$ Copolypeptide

A diblock copolypeptide, poly(L-lysine$_{200}$-b-L-cysteine$_{30}$) or "Lys$_{200}$Cys$_{30}$" (FIG. 1) was synthesized and used to direct the assembly of Au/SiO$_2$ hybrid spheres. A Lys$_{200}$Cys$_{30}$ (MW=28,890, HBr salt form) solution was prepared for a final concentration of 2.5 mg/ml. 125 µl of a sol containing Au nanoparticles ("n-Au," 9.4 µmol-particle/L) was added to 50 µl of the polymer solution. The color of the Au sol changed from ruby red to violet purple after addition, indicating the n-Au particles underwent aggregation that redshifts the plasmon resonance frequency. After 5 minutes of aging with occasional agitation, 125 µl of a sol containing SiO$_2$ nanoparticles ("n-SiO$_2$," 360.1 µmol-particle/L) was next added, causing the clear, purplish solution to become a turbid, purplish solution. After about 15 minutes, a purple precipitation was observed and after 24 hours, a purple floe was found at the vial bottom. This precipitate was composed of large spherical objects that appeared to have a hollow center (FIG. 1). FIG. 3 depicts a schematic of a proposed formation mechanism of these hybrid nanoparticle assembled hollow spheres.

A scanning electron microscopy (SEM) image of the n-Au/n-SiO$_2$/Lys$_{200}$Cys$_{30}$ showed nearly exclusively spheres (FIG. 8a). The sphere diameters ranged from 500 nm to 3 µm. A TEM of the same material is shown on the same scale (FIG. 8b). Some other shapes were also observed, such as spheres with a single dimple ("apples") and spheres with an opening ("cups").

Example 2

Using Different n-Au and n-SiO$_2$ Amounts

The effect of relative ratios of n-Au and n-SiO$_2$ particles to a fixed amount of copolypeptide concentration was studied. With Example 1 as the base sample (center image, FIG. 4e), 8 samples were prepared using 10 times more or less n-Au sol and 10 times more or less n-SiO$_2$ sol. The samples were examined via SEM 12 days after their preparation. According to SEM results, 10×less n-Au did not lead to any defined microparticles for all amounts of n-SiO$_2$, suggesting that a certain minimum amount of Au nanoparticles is required for the hybrid spheres to form (FIGS. 4a-c). When 10× less n-SiO$_2$ was used, using 10×more n-Au appeared to give same-size, more aggregated microparticles (FIG. 4g), as using 1×amount of n-Au (FIG. 4d). When 1×amount of n-SiO$_2$ was used, however, the aggregates were much larger (FIG. 4e). The aggregates for the 10×more n-Au were roughly the same size but they looked like cups rather than spheres (FIG. 4h). Using 10×more n-SiO$_2$ led to Swiss cheese-like films (FIGS. 4f and 4i).

Example 3 n-Au/n-SiO$_2$/Lys$_{200}$Cys$_{30}$ Films n-Au/n-SiO$_2$/Lys$_{200}$Cys$_{30}$ spheres can be prepared in highly aggregated form (FIG. 9). Hybrid spheres were in contact with one another as a network (FIG. 9(a)) and as a packed film (FIG. 6(b)). While about 20 nm Au nanoparticles were used instead of the 10-12 nm particles of Example 1, production of the film is likely due to a lower ratio of n-Au to copolypeptide.

Example 4

Figure 10A:
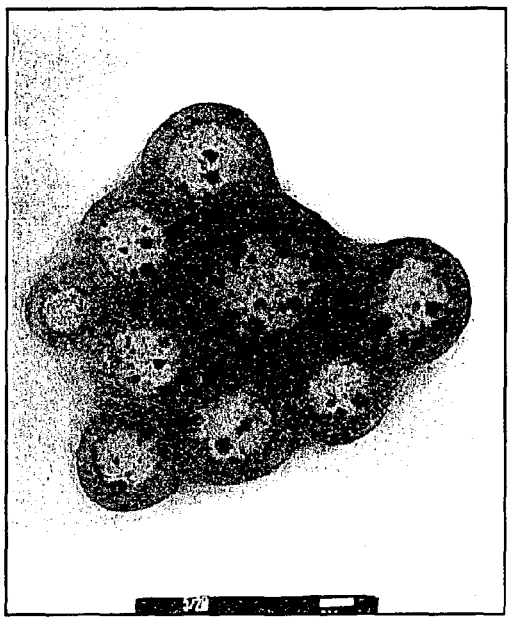
FIG. 10a-b are TEM images of n-Ag/n-SiO$_2$/Lys$_{200}$Cys$_{30}$ as an aggregate of spheres (FIG. 7a) and an isolated apple (FIG. 7b).
Figure 10B:
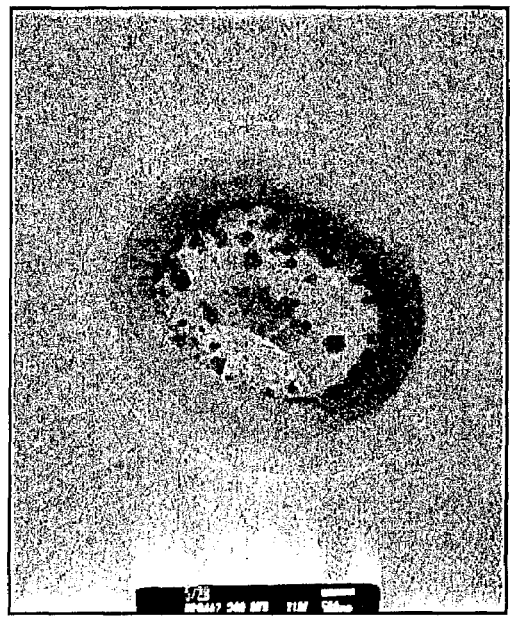

Using Different Nanoparticles for the Interior n-Ag/n-SiO$_2$/Lys$_{200}$Cys$_{30}$ spheres were produced by using a n-Ag sol instead of the n-Au sol (FIG. 10). A n-Ag sol (diameter about 4 nm) was produced sonochemically.

Example 5

Figure 11:
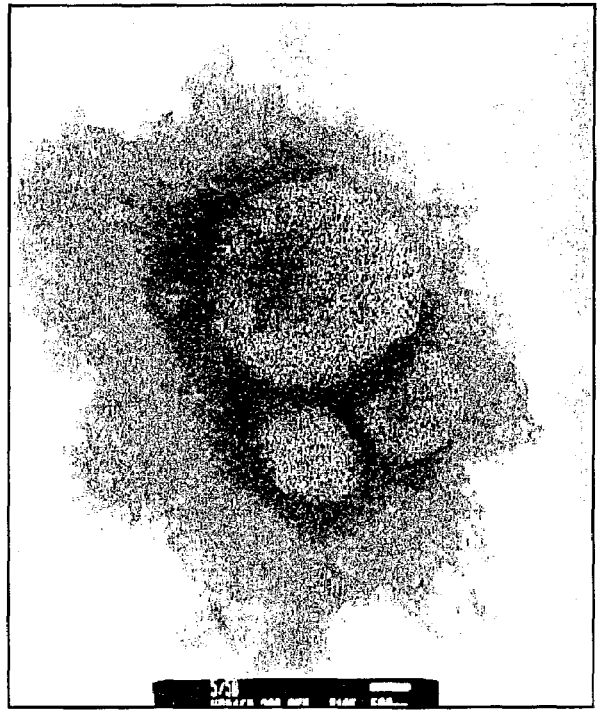
FIG. 11 is a TEM image of n-Ag/n-CdSe/Lys$_{200}$Cys$_{30}$

Using Different Nanoparticles for the Shell n-Au/n-CdSe/Lys$_{200}$Cys$_{30}$ spheres were produced by using a n-CdSe sol instead of the n-SiO$_2$ sol (FIG. 11). CdSe nanoparticles, or quantum dots (QD's), were prepared through pyrolytic decomposition of a cadmium and selenium precursors to give particle size ~4 nm, in a process invented by Wong and Stucky [Wong and Stucky, 2001]. The QD's were soluble in organic solvents and were made soluble in citrate buffer aqueous solution by functionalizing the QD surface with mercaptosulfonic acid (sodium salt, Aldrich). The buffer solution contained the mercapto compound and added to a volume of QD's to create a two-phase mixture. Shaking the mixture and letting sit overnight caused complete phase transfer of the QD's from the methylene chloride phase to the water phase, as indicated by the red color of the water phase. A small amount of this n-CdSe containing solution was added in lieu of the n-SiO$_2$ sol.

Example 6

Using Homopolymer Polyelectrolytes as Structure-Directing Agents

Materials and Methods

Homopolymer polyelectrolytes. The only homopolymer synthesized was poly-L-lysine HBr; all other polyelectrolytes (including a control poly-L-lysine) were purchased from either Sigma-Aldrich (molecular weight range from 25,000-60,000) or PolySciences. Poly-L-lysine$_{100}$, poly-L-lysine$_{200}$ and poly-L-lysine$_{300}$ were synthesized from N$_\epsilon$-carboxybenzyl-L-lysine N-carboxyanhydrides and the initiator 2,2'-bipyridyl-Ni(1,5-cyclooctadiene)[25] with polydispersities ranging from 1.05 to 1.2. The CBZ-L-lysine polymers were then deprotected to give the free amine functional group using a mixture of trifluoroacetic and hydrobromic acid, the excess of which was later removed by dialysis.

Negatively charged nanoparticles. Silica and citrate coated gold nanoparticles were used as described previously.[26] The water-soluble, citrate stabilized quantum dots were synthesized as previously reported by Kotov and co-workers.[27] Two final sets of quantum dots corresponding to green and orange-red emission were used for the vesicle assembly. The synthesized quantum dots were characterized by transmission electron microscopy (TEM) as well as absorbance and fluorescence measurements.

Nanoparticle Vesicle Assembly. The polyelectrolyte solutions were, regardless of molecular weight, prepared at concentrations of 5 mg/ml. 100 μl of the as-synthesized quantum dot solution was first diluted to 200 μl total volume with deionized water. The 200-μl quantum dot aliquot was then added to 50 μl of the polyelectrolyte solution. The reaction was vigorously mixed by manually pipetting, during which the solution altered in turbidity from a cloudy suspension to a macroscopically clear solution. The vesicles were imaged using both bright field and fluorescence optical microscopy; the fluorescence images were done using a continuous wave (CW) argon ion 365-nm laser line.

Dynamic light scattering measurements of the nanoparticle vesicles. All nanoparticle vesicles were prepared immediately prior to measurements. Dynamic light scattering measurements were made on a Brookhaven Instruments BI-9000AT Digital Correlator as a function of scattering angle (40-130°) at room temperature with sampling delay times from 1 μs to 10 s. The raw data were analyzed by least-squares fits to a cumulant expansion to which two additional long decays were added:

$$a_0 + a_1 \exp(-2k_1\tau + k_2\tau^2 - (1/3)k_3\tau^3) + a_2 \exp(-2k_{21}\tau) + a_3 \exp(-2k_{31}\tau).$$

The two long-decay-rate mono-exponential functions were included to model very large assemblies, probably arising from conglomerates of spherical assemblies and/or the presence of dust. The hydrodynamic radius, $R_H$, of the spheres was extracted by fitting the Stokes expression to the decay rate constants:

$$\Gamma = k_1 = q^2 D = q^2 T k_B / 6\pi \eta R_H.$$

This gives $R_H = 1.5$ μm.

Hollow Sphere Synthesis. The silica CdSe quantum dot hollow spheres were generated by adding 200 μl of commercially available colloidal silica, Snowtex 0, to the already formed nanoparticle vesicle solutions. The hollow spheres were allowed to settle to the bottom of the eppendorf tubes before characterization by optical and electron (scanning electron microscopy (SEM) and TEM) microscopy. A similar procedure can be used with citrate-coated gold nanoparticles replacing the semiconductor quantum dots.

Results and Discussion

The repeating unit of the cationic, amino acid based polyelectrolyte, poly-L-lysine (Table 1, P1), is a primary amine with a corresponding pKa of ~10.5. Poly-L-lysine of different chain lengths showing a monodispersity of less than 1.1 were synthesized from N$_\epsilon$-carboxybenzyl-L-lysine-N-carboxyanhydride monomers and the initiator 2,2'-bipyridyl-Ni(1,5-cyclooctadiene). The hydrochoride and hydrobromide salts of poly-L-lysine, poly-L-arginine and polyallylamine were also commercially purchased for comparison experiments. Water-soluble, citrate-stabilized cadmium selenide (CdSe) quantum dots were first synthesized as reported by Kotov and co-workers[27] and used to titrate at pH 7.5 aqueous solutions of the cationic poly-L-lysine (0.5 to 1.0 mg/ml).

The addition of citrate-stabilized CdSe quantum dots to the poly-L-lysine solutions caused the initial transparent polymer mixtures to become visibly turbid and cloudy, indicating aggregation of the positively charged polypeptide with the negatively charged nanoparticles. However, upon continued mixing, the solutions changed from cloudy to clear, and light microscopy imaging revealed what looked like oil droplets in an aqueous medium (FIG. 5A). Dynamic light scattering measurements (FIG. 5B) were done on the assembled nanoparticle vesicles and the measured effective diameters of approximately 3.0 μm corresponded to those seen by optical microscopy. While the as-assembled nanoparticle vesicles collapsed upon air drying, the addition of silica nanoparticles produced stable three-dimensional hollow spheres where the shell walls were formed of a distinct inner layer of CdSe quantum dots surrounded by a thinner outer layer of silica nanoparticles (FIG. 6).

The formation of these vesicles was discovered to be stringently dependent on the overall molar charge ratios of the negative citrate molecules to the positive amines of poly-L-lysine. The allowed window was narrow and determined to be between 0.30 and 0.40 (negative citrate charges to positive amine charges). At ratios below 0.3, the addition of citrate stabilized quantum dots created no cloudiness or emulsions to form, and at ratios above 0.4, the solutions turned initially cloudy followed by a rapid precipitation that consisted of both nanoparticles and polymer. At high ratios of nanoparticles to polymer, substantial charge matching between the negative citrate and positive amine groups causes insolubility to occur.

As a way to further elucidate the molecular chemistry occurring at the interface between the nanoparticles and the polyelectrolyte, quantum dots with other negatively charged stabilizing ligands were synthesized and reacted with poly-L-lysine. Water-soluble negatively charged tri-octylphosphine (TOPO) stabilized CdSe quantum dots were produced using a reported surface exchange method with mercaptoacetic acid.[29] These TOPO-mercaptoacetic acid functionalized quantum dots were then mixed with solutions of poly-L-lysine, but unlike the results obtained using the citrate functionalized quantum dots, no vesicles or any other observable supramolecular organization of the nanoparticles was detected.

An additional set of experiments was next performed where a different cationic, amino acid based polyamine, poly-L-arginine (pKa ~12.5), was reacted with the citrate stabilized quantum dots. Surprisingly, upon using similar polymer chain length dimensions and working concentrations as those used for poly-L-lysine, the addition of citrate-stabilized CdSe nanoparticles only caused the poly-L-arginine solutions to become turbid with no ensuing phase transition into vesicles. Electron microscopy of the final products showed no vesicular geometries and only coagulated materials. However, the non-amino acid based polyamine, poly(allylamine hydrochloride) spontaneously produced nanoparticle vesicles when mixed with the citrate-functionalized CdSe quantum dots. Nevertheless, the striking differences in products obtained between using the cationic polypeptides, poly-L-lysine and poly-L-arginine (which is more highly ionized than poly-L-lysine) determined that the molecular interactions controlling the poly-L-lysine nanoparticle vesicles was a directionalized bonding coordination between the amines of the polymer and the carboxylic acid group of the quantum dots.

The initial part of the synthesis of the citrate stabilized CdSe nanoparticles involves the complexation of free $Cd^{2+}$ ions with citrate molecules in water at pH 9.0. From the three relative pKa values of citric acid, it can be deduced that the $Cd^{2+}$ ions are binding the carboxylic acid groups with the two lowest pKa values, specifically 3.8 ($pK_1$) (Table 1, C1) and 4.6 ($pK_2$) (Table 1, C2). This binding scheme is in accordance with the observed behavior of $Al^{III}$, $Ga^{III\ 30}$ and $Zn^{II\ 31}$ in obtained crystal structures. The final CdS/CdSe core shell quantum dots are then structured such that the only surface-accessible carboxylic acid group is that corresponding to the most basic pKa of 6.3 ($pK_3$) (Table 1, C3) and that it is this specific functionality that interacts with the primary amine of poly-L-lysine.

Example 7

Designed Microsphere Delivery Parameters

A critical feature of therapeutic agent delivery is the ability to deliver the contents upon arrival at a cellular destination. For example, if therapeutic agent delivery was required to the vagina, the pH of the vaginal secretions (pH 3.5-4.5) (37) would allow the opening of the microspheres. Delivery of therapeutic reagents could also be accomplished in the lining of the stomach because of the low pH in that organ (38). Interestingly, this method may also work for absorption of any therapeutic agent for delivery into the bloodstream. In addition, the vascular supply to tumors is often poorly formed resulting in a poor nutritional supply, hypoxia and acidic pH (39), and this delivery method would allow targeted delivery to cancer cells because of the proteins on microsphere's exterior would allow targeting, and then delivery would occur because of the cancer cells' acidic microenvironment's ability to open the microsphere. Microspheres in accordance with preferred embodiments of the present invention can be opened upon entry into a changed ionic chemical environment because of the charge distribution dependence on microsphere formation. In order to elucidate and characterize this further, careful pH experiments were performed. As demonstrated in Table 1, the spontaneous formation of nanoparticle vesicles depends on both the pKa of citric acid (6.3) and the pKa of the poly-L-lysine (10.5) that is present in both the diblock copolypeptide and the polylysine polymer. At pH values below 6.5 and above 11, the pre-assembled microspheres opened to present their contents, thus allowing therapeutic delivery (see Table 1). This sensitivity to pH was non-linear; when the pH values of the vesicle solutions were changed to either below 6 or above 11, the vesicles opened. This observation is of particular interest with respect to the use of these microspheres for the pH controlled transport and delivery of encapsulated contents. Furthermore, the pH window can be adjusted and tuned by the use of modifications of the polyelectrolyte and particle capping agent.

TABLE 1

Vesicle opening upon pH changes.

| pH of Citrate capped nanoparticle | pH of poly-L-lysine | Vesicle Opening |
| --- | --- | --- |
| 5.0 | 7.0 | Yes |
| 5.5 | 7.0 | Yes |
| 6.0 | 7.0 | Yes |
| 6.5 | 7.0 | No |
| 7.0 | 7.0 | No |
| 8.0 | 7.0 | No |
| 9.0 | 7.0 | No |
| 9.5 | 7.0 | No |
| 7.0 | 12.0 | Yes |

Microsphere opening was also subjected to a NaCl gradient, and the assembled microspheres remained intact up to 40 mM NaCl. Preliminary light scattering data reveal that the vesicles remain intact up until 250 mM NaCl (Birkedal, H., Cha, J., and Stucky, G., unpublished observations) suggesting direct bonding interactions between the ligands on the nanoparticles and the polymer. Using this self-assembly mechanism allows an unusual stability to high salt concentrations.

REFERENCES

1 D. Lechardeur and G. L. Lukacs, Curr. Gene Ther. 2 (2), 183 (2002).
2 M. W. Sung, S. G. Lee, S. J. Yoon, H. J. Lee, D. S. Heo, K. H. Kim, T. Y. Koh, S. H. Choi, S. W. Park, J. W. Koo, and T. Y. Kwon, Anticancer Res. 20 (3A), 1653 (2000).
3 J. A. Zasadzinski, E. Kisak, and C. Evans, Current Opinion in Colloid & Interface Science 6 (1), 85 (2001).
4 M. Kokkona, P. Kallinteri, D. Fatouros, and S. G. Antimisiaris, Eur. J. Pharm. Sci. 9 (3), 245 (2000).
5 K. Bogunia-Kubik and M. Sugisaka, Biosystems 65 (2-3), 123 (2002).
6 S. R. Sershen, S. L. Westcott, H. N. J., and J. L. West, J. Biomed. Mater. Res. 51 (3), 293 (2000).
7 S. Terrettaz, W. P. Ulrich, H. Vogel, Q. Hong, L. G. Dover, and J. H. Lakey, Protein Sci. 11 (8), 1917 (2002).
8 Y. Tabata, Y. Murakami, and Y. Ikada, Jpn. J. Cancer Res. 88 (11), 1108 (1997).
9 B. C. Braden, F. A. Goldbaum, B. X. Chen, A. N. Kirschner, S. R. Wilson, and B. F. Erlanger, Proc. Natl Acad. Sci. USA 97 (22), 12193 (2000).
10 R. F. Schinazi, R. Sijbesma, G. Srdanov, C. L. Hill, and F. Wudl, Antimicrob. Agents Chemother. 37 (8), 1707 (1993).
11 A. P. Alivisatos, Science 271, 933 (1996).
12 C. A. Mirkin, R. L. Letsinger, R. C. Mucic, and J. J. Storhoff, Nature 382, 607 (1996).
13 A. K. Boal, F. Ilhan, J. E. DeRouchey, T. Thurn-Albrecht, T. P. Russell, and V. M. Rotello, Nature 404, 746 (2000).
14 W. Shenton, S. A. Davis, and S. Mann, Adv. Mater. 11, 449 (1999).
15 *MRS Proc.*, edited by D. L. Wilcox, Sr., M. Berg, T. Bernat, D. Kellerman, and J. K. Cochran, Jr. (Materials Research Society, Pittsburgh, 1995), Vol. 372.
16 L. C. Brousseau, III, J. P. Novak, S. M. Marinakos, and D. L. Feldheim, Adv. Mater. 11, 447 (1999).
17 Z. Zhong, Y. Yin, B. Gates, and Y. Xia, Adv. Mater. 12, 206 (2000).
18 P. Jiang, J. F. Bertone, and V. L. Colvin, Science 291, 453 (2001).

19 M. S. Wong, J. H. Cha, K. -S. Choi, T. J. Deming, and G. D. Stucky, Nano Letters 2, 583 (2002).

20 T. J. Deming, Nature 390 (6658), 386 (1997).

21 M. Bruchez, Jr., M. Moronne, P. Gin, S. Weiss, and A. P. Alivisatos, Science 281, 2013 (1998); H. J. Eisler, V. C. Sundar, M. G. Bawendi, M. Walsh, H. I. Smith, and V. Klimov, Appl. Phys. Lett. 80 (24), 4614 (2002); W. U. Huynh, J. J. Dittmer, and A. P. Alivisatos, Science 295, 2425 (2002).

22 M. Kazes, D. Y. Lewis, Y. Ebenstein, T. Mokari, and U. Banin, Adv. Mater. 14, 317 (2002).

23 V. I. Klimov, A. A. Mikhailovsky, S. Xu, A. Malko, J. A. Hollingsworth, C. A. Leatherdale, H. -J. Eisler, and M. G. Bawendi, Science 290, 314 (2000).

24 H. Yokoyama, Science 256, 66 (1992).

25 M. Pelton and Y. Yamamoto, Phys. Rev. A 59, 2418 (1999); V. I. Klimov and M. G. Bawendi, MRS Bulletin 26, 998 (2001); X. D. Fan, M. C. Lonergan, Y. Z. Zhang, and H. L. Wang, Phys. Rev. B 64, 115310 (2001); M. V. Artemyev and U. Woggon, Appl. Phys. Lett. 76 (11), 1353 (2000).

26 M. V. Artemyev, U. Woggon, R. Wannemacher, H. Jaschinski, and W. Langbein, Nano Lett. 1 (6), 309 (2001).

27 J. N. Cha, H. Birkedal, M. H. Bartl, M. S. Wong, and G. D. Stucky, J. Am. Chem. Soc., submitted (2002).

28 S. Schacht, Q. Huo, I. G. Voigt-Martin, G. D. Stucky, and F. Schüth, Science 273 (5276, August 9), 768 (1996); Q. Huo, J. Feng, F. Schüth, and G. D. Stucky, Chem. Mater. 9, 14 (1997); G. D. Stucky, Q. Huo, A. Firouzi, B. F. Chmelka, S. Schacht, I. G. Voigt-Martin, and F. Schüth, in *Progress in Zeolite and Microporous Materials* (*Studies in Surface Science and Catalysis* 105), edited by H. Chon, S. -K. Ihm, and Y. S. Uh (Elsevier, Amsterdam, 1997), pp. 3; A. M. Belcher, C. Zaremba, Q. Huo, C. C. Landry, S. H. Tolbert, A. Firouzi, M. Janicke, P. K. Hansma, D. E. Morse, B. F. Chmelka, S. Schacht, I. G. Voigt-Martin, F. Schüth, and G. D. Stucky, in *Chemistry on the Nanometer Scale, Proc. 40th Robert A. Welch Foundation Conference on Chemical Research* (Robert A. Welch Foundation, Houston Tex., 1996), pp. 101; C. Yu, B. Tian, G. D. Stucky, and D. Zhao, Chem. Lett., 62 (2002).

29 J. N. Cha, G. D. Stucky, D. E. Morse, and T. J. Deming, Nature 403 (6767), 289 (2000).

What is claimed is:

1. A nanoparticle-containing microsphere comprising:
   a. A diblock copolymer, acting as structure directing agent, that binds to a first and second type of nanoparticles; wherein the copolymer comprises a peptide block having a sequence of about 10-400 positively-charged residues selected from a group consisting of lysine, arginine, and histidine, and a peptide block of about 10-400 cysteine residues;
   b. the structure of the agent being such to direct the formation of an inner and outer layer of said microsphere;
   c. said inner layer of said microsphere comprising a first type of nanoparticles bound to the cysteine residues of the structure directing agent; and
   d. said outer layer of said microsphere coating the inner layer comprising a second type of nanoparticles bound to the positively charged residues of the structure-directing agent;
   e. wherein the first type of nanoparticles is selected from the group consisting of semiconductor group II-VI metal non-oxide nanocrystals, gold nanoparticles, silver nanoparticles, platinum nanoparticles, palladium nanoparticles, copper nanoparticles, rhodium nanoparticles, rhenium nanoparticles, nickel nanoparticles, and iridium nanoparticles and primary functionalization thereof to introduce therapeutic or imaging agents; and
   f. wherein the second type of nanoparticles is selected from the group consisting of silicon oxide, titanium oxide; aluminum oxide, zirconium oxide, magnesium oxide and-secondary functionalization thereof to introduce a recognition element for in vivo targeting.

2. A nanoparticle-containing microsphere comprising:
   a. poly-L-lysine 100-300 or poly(allylamine hydrochloride), acting as structure directing agent, that binds to a first and second type of nanoparticles;
   b. the structure of the agent being such to direct the formation of an inner and outer layer of said microsphere;
   c. said inner layer of said microsphere comprising a first type of nanoparticles bound to a portion of the structure directing agent; and
   d. said outer layer of said microsphere coating the inner layer comprising a second type of nanoparticles bound to another portion of the structure-directing agent;
   e. wherein the first type of nanoparticles is selected from the group consisting of group II-IV semiconductor nanocrystals, gold nanoparticles, silver nanoparticles, platinum nanoparticles, palladium nanoparticles, copper nanoparticles, rhodium nanoparticles, rhenium nanoparticles, nickel nanoparticles, and iridium nanoparticles and primary functionalization thereof to introduce therapeutic or imaging agents; and
   f. wherein the second type of nanoparticles is selected from the group consisting of silicon oxide, titanium oxide; aluminum oxide, zirconium oxide, magnesium oxide, and secondary functionalization thereof to introduce a recognition element for in vivo targeting.

3. A method of making a nanoparticle-containing microsphere comprising:
   a) combining a solution of a diblock copolypeptide, wherein the diblock acts as structure-directing agent, that binds to a first and second type of nanoparticles and directs the formation of an inner and outer layer of said microsphere, wherein the copolypeptide comprises a peptide block having a sequence of about 10-400 positively-charged residues selected from a group consisting of lysine, arginine, and histidine, and a peptide block of about 10-400 cysteine residues;
   b) with a solution of a first type of nanoparticles for a time and under conditions sufficient for the first type of nanoparticles to bind to the cysteine residues portion of the structure directing agent and self assemble into an inner shell; and
   c) adding a solution of a second type of nanoparticles, to the diblock and first type of nanoparticle mixture, of a different type than the first type of nanoparticles, under conditions sufficient for the second type of nanoparticles to bind to the positively charged residue portion of the structure-directing agent and for the second type of nanoparticles to form an outer layer coating the inner layer containing the first type of nanoparticles;
   wherein the first type of nanoparticles is selected from the group consisting of semiconductor group II-VI metal non-oxide nanocrystals, gold nanoparticles, silver nanoparticles, platinum nanoparticles, palladium nanoparticles, copper nanoparticles, rhodium nanoparticles, rhenium nanoparticles, nickel nanoparticles, and iridium nanoparticles and primary functionalization thereof to introduce therapeutic or imaging agents; and
   wherein the second type of nanoparticles is selected from the group consisting of silicon oxide, titanium oxide;

aluminum oxide, zirconium oxide, magnesium oxide and secondary functionalization thereof to introduce a recognition element for in vivo targeting.

4. The method of claim 3, further comprising performing a calcination step to remove the structure-directing agent.

5. The method of claim 3, further comprising mixing either one or both of the first and second type of nanoparticles with a citrate solution.

6. A method of making a nanoparticle-containing microsphere comprising:
   a) combining a solution of poly-L-lysine 100-300 or poly (allylamine hydrochloride),
   wherein the poly-L-lysine 100-300 or poly(allylamine hydrochloride) acts as structure-directing agent, that binds to a first and second type of nanoparticles and directs the formation of an inner and outer layer of said microsphere,
   with a solution of a first type of nanoparticles for a time and under conditions sufficient for the first type of nanoparticles to bind portion of the structure directing agent and self assemble into an inner shell; and
   b) adding a solution of a second type of nanoparticles, to the diblock and first type of nanoparticle mixture, of a different type than the first type of nanoparticles, under conditions sufficient for the second type of nanoparticles to bind to another portion of the structure-directing agent and for the second type of nanoparticles to form an outer layer coating the inner layer containing the first type of nanoparticles;
   wherein the first type of nanoparticles is selected from the group consisting of group II-IV semiconductor nanocrystals, gold nanoparticles, silver nanoparticles, platinum nanoparticles, palladium nanoparticles, copper nanoparticles, rhodium nanoparticles, rhenium nanoparticles, nickel nanoparticles, and iridium nanoparticles and primary functionalization thereof to introduce therapeutic or imaging agents; and
   wherein the second type of nanoparticles is selected from the group consisting of silicon oxide, titanium oxide; aluminum oxide, zirconium oxide, magnesium oxide, and secondary functionalization thereof to introduce a recognition element for in vivo targeting.

* * * * *